United States Patent [19]

Ogura et al.

[11] 4,447,600
[45] May 8, 1984

[54] N-ACETYLNEURAMINIC ACID DERIVATIVES AND THE PREPARATION THEREOF

[75] Inventors: Haruo Ogura, Matsudo; Kimio Furuhata, Tokyo; Toshiaki Osawa, Akatsukashin; Satoshi Toyoshima, Tokyo; Yoshiyasu Shitori, Musashino; Masayoshi Ito, Kunitachi, all of Japan

[73] Assignee: Kanto Ishi Pharmaceutical Co., Ltd., Japan

[21] Appl. No.: 380,401

[22] Filed: May 20, 1982

[30] Foreign Application Priority Data

May 22, 1981 [JP] Japan .................................. 56-77672

[51] Int. Cl.$^3$ ............................................ C07H 17/00
[52] U.S. Cl. ......................................... 536/23; 536/24
[58] Field of Search ........................... 536/24, 23, 17.9

[56] References Cited

U.S. PATENT DOCUMENTS 3,308,117  3/1967  Kelly et al. ........................... 536/24
4,202,968  5/1980  Tamura et al. ....................... 536/23

*Primary Examiner*—Ethel G. Love
*Attorney, Agent, or Firm*—Jacobs & Jacobs

[57] ABSTRACT

Nucleoside or glucose derivatives of N-acetylneuraminic acids are provided, which have immunological activity, are clinically useful, as an immuno suppressive, in particular to treat autoimmune disease such as collagenosis disease without causing any serious side-effects and may be prepared by subjecting a halide of N-acetylneuraminate derivative together with a nucleoside or a glucose to Koenigs-Knorr reaction.

5 Claims, No Drawings

N-ACETYLNEURAMINIC ACID DERIVATIVES AND THE PREPARATION THEREOF

BACKGROUND OF THE INVENTION

The present invention relates to new N-acetylneuraminic acid derivatives, in particular to those having immunological activity and a method of the preparation thereof.

It has been known that N-acetylneuraminic acid exists in animals and on the cell surface of some bacteria as sialocomplex (glycoproteins, glycolipids, oligosaccharides, polysaccharides). Recently, it has been recognized that this compound is important medically and pharmaceutically in conditioning the function of nerve system, differentiation of cells and immunity, treatment of inflammatory, cancer, virus infection and as a hormone receptor and the compound has drawn attention to as a specific active molecule localized on the cell surface.

However, the roles of this compound in the sialocomplex are still a matter of conjecture.

A number of organic chemists who engage in the investigation of natural substances studied this compound and they reported various kind of simple derivatives thereof [see, for example, J. Biol. Chem., 244, 1306 (1969); Z. Physiol. Chem., 352, 1715 (1971)]. However, no derivative having a conspicuous physiological activity has yet been known.

Owing to the recently developed multilateral treatments for diseases such as every kind of cancer inclusive of malignant tumour of the hematogenic organs and collagenosis diseases, an apothanasia effect is, in fact, attained. While, an immoderate use of adrenocortical hormones and immunosuppressors is almost inevitable and therefore, the problem of side-effects as well as the reduction or decrease in so-called capacity of immunity are matter of grave concern.

Therefore, there is a strong demand for more safer and more effective medicines which causes no entrainment of serious side-effects.

SUMMARY OF THE INVENTION

Under such circumstances, the inventors of the present invention exhaustively studied and investigated to obtain N-acetylneuraminic acid derivatives having a higher immunological activity without entraining any serious side-effects and found that the above-mentioned disadvantages could be eliminated by chemically modifying N-acetylneuraminic acid with a sialic acid which is inherent component of the living body. Thus, the inventors completed this invention.

The principal object of this invention is to provide new N-acetylneuraminic acid derivatives, in particular those having a high immunological activity without causing any side-effects.

Another object of this invention is to provide a method of preparing said new N-acetylneuraminic acid derivatives.

The said and other objects as well as features of the present invention will be more apparent from the following detailed description.

DETAILED DESCRIPTION OF THE INVENTION

New N-acetylneuraminic acid derivatives according to the present invention are represented by the following general formula [I]:

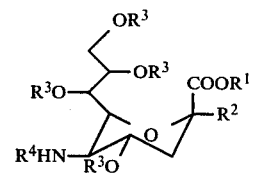

wherein $R^1$ represents H, a lower alkyl, or a lower alkyl substituted or non-substituted aralkyl or aryl group, $R^2$ stands for a residue of a nucleoside or a glucose and $R^3$ and $R^4$ represent H or acetyl group independently.

According to the present invention, the term "lower alkyl" means methyl or ethyl group preferably.

The term "nucleoside residue" used in the present invention means a residue in which a saccharide and a purine or a pyrimidine base are bonded with glycoside bond, and these residues may include a substituent or substituents and/or condensed rings. The basic backbone of these residues are represented by the following structural formula:

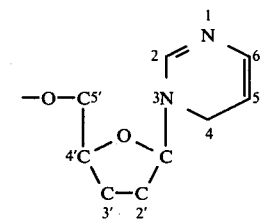

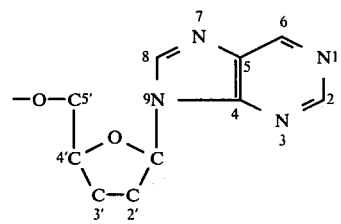

The following residues, for example, may preferably be used:

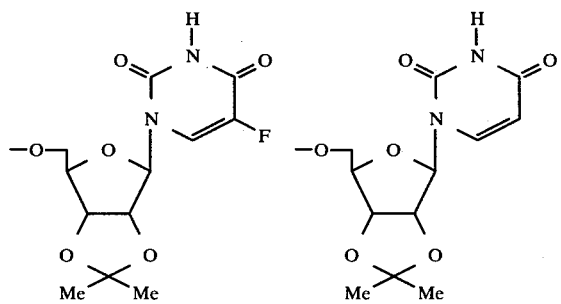

-continued

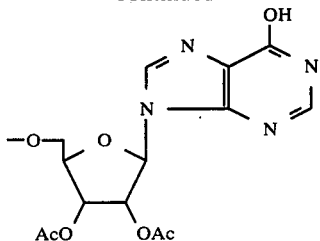

The term "glucose residue" herein used includes residues D- and L- type, in particular D-glucose residue being preferably used. The following residues are the typical ones:

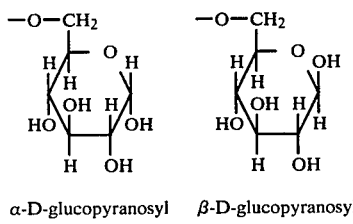

α-D-glucopyranosyl  β-D-glucopyranosyl

The said term also includes the residues in which part of or all of the hydroxy groups are esterified with for example acetic acid:

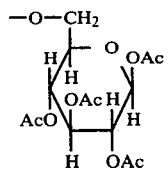

The new N-acetylneuraminic acid derivatives of this invention may be prepared according to process which comprises subjecting a compound of the formula [II]:

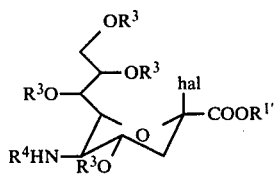

[II]

wherein $R^{1'}$ stands for a lower alkyl or a lower alkyl substituted or non-substituted aralkyl or aryl group, $R^3$ and $R^4$ are hydrogen atom or acetyl group independently and hal represents a halogen atom, and a nucleoside or a glucose hereinbefore defined to Koenigs-Knorr reaction, and then if desired deacetylating the resulting product.

In the Koenigs-Knorr reaction, we may use, for example $Ag_2CO_3$, $Ag_2O$, $Hg(CN)_2$, $HgBr_2$, $AgClO_4$ as a catalyst, and in a preferred embodiment it is effective in using a molecular sieve such as molecular sieve 3A and 4A together with a catalyst so as to effectively remove hydrogen halides generated during the reaction, enhancing the reaction rate and improving the yield of the reaction product.

Although there is no critical range in the reaction temperature, the reaction is usually carried out at room temperature from the economical point of view and the simplicity of the operation.

The reaction period is in a range of from 30 minutes to 24 hours.

Acetonitrile or nitromethane may preferably be used as a reaction medium in the present invention.

The deacetylation reaction may be carried out according to a process which comprises agitating the product having acetyl group(s), obtained after the Koenigs-Knorr reaction, at a temperature of −20° to 0° C. for about 20 minutes in a reaction medium such as methanol, under the presence of an alkali metal alcoholate, neutralizing the reaction solution with Dowex 50×8 (H+) and thereafter treating the product according to a conventional procedures.

Preferred examples of the process for preparing new N-acetylneuraminic acid derivatives are hereinafter illustrated as a reaction formula.

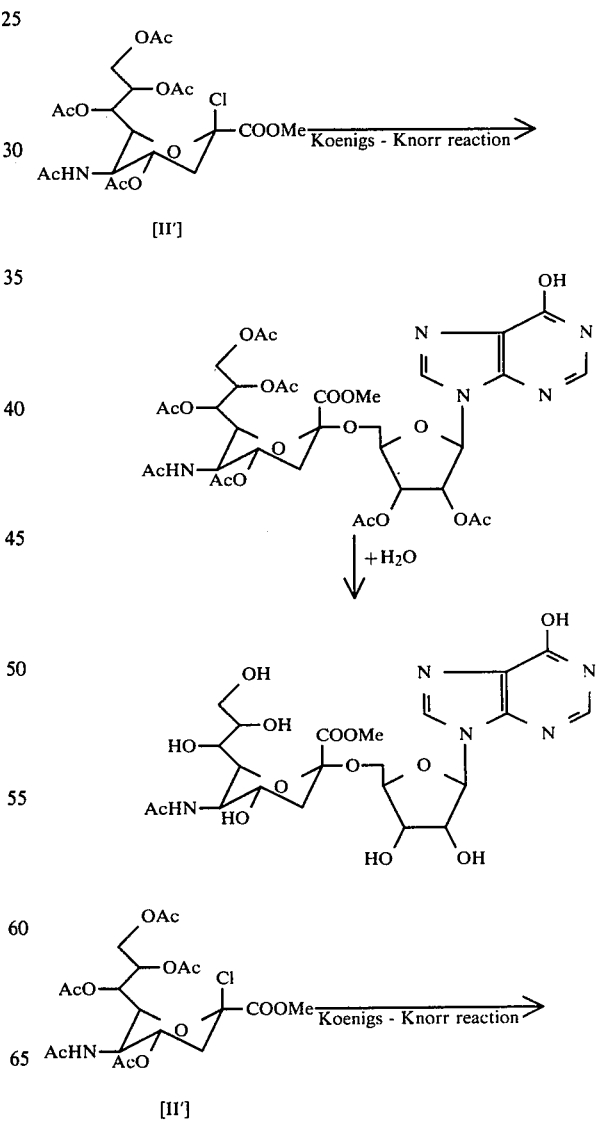

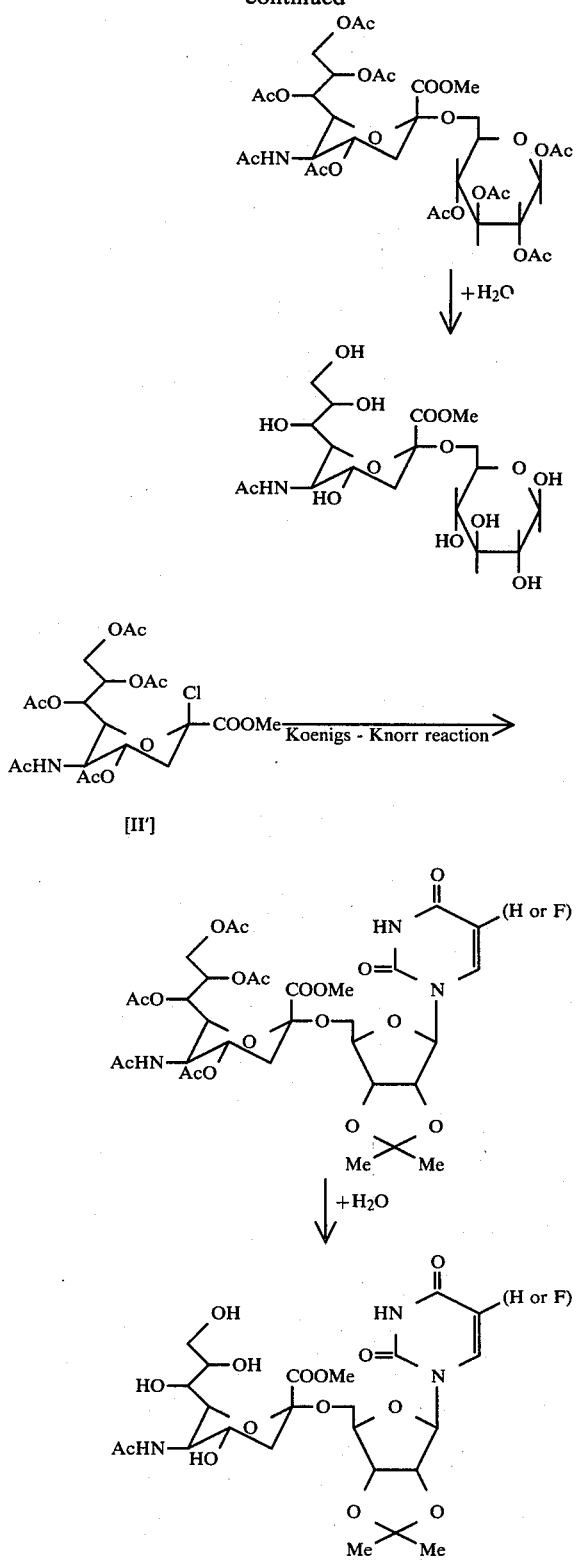

The compounds [I] of the present invention have a remarkable activity respectively for conditioning immunity.

The immunological functions may be determined according to the following process:

(i) Effect on the activation of murine splenic lymphocytes with Con A

Suppressor T cells are non-specifically activated by Concanavalin A (Con A). Then, we investigated effects of N-acetylneuraminic acid derivatives of the invention on said reaction system. The investigation was carried out according to the following procedure. Firstly, Con A and each one of the compound [I] were added to splenic lymphocytes (SPC) obtained from BALB/C mice to prepare samples. These samples were cultured on a microplate at 37° C. for 20 hours in a 5% $CO_2$ atmosphere, then tritium labeled thymidine was added to the samples and the samples were cultured at 37° C. for another 18 hours. Then, the SPC was collected and the amount of $^3H$-thymidine incorporated into the SPC was determined by using a scintillation counter.

As a result, it was observed that the incorporation of $^3H$-thymidine into SPC was accelerated and enhanced and that the activation of T cells by Con A was also enhanced with the presence of the compounds [I] of the present invention. Results on typical compounds are shown in Table 1.

TABLE 1

Effect of neuraminic acid derivatives on the DNA Synthesis of Con A-Stimulated lymphocytes

| Derivative | Concentration (M) | Stimulation Index of [6-$^3$H] Thymidin Incorporation[a] | |
|---|---|---|---|
| | | With Con A | Without Con A |
| None | | 1.00 | 1.00 |
| Compound [II'] | $10^{-4}$ | 1.10 | 0.93 |
| Compound [Ex. 8] | $10^{-5}$ | 1.57 | 1.26 |
| Compound [Ex. 9] | $10^{-4}$ | 1.81 | 1.24 |
| FIU | $10^{-5}$ | 0.02 | 0.47 |
| DAI | $10^{-4}$ | 1.07 | 1.24 |
| Compound [II'] + FIU | $10^{-5}$ | 0.02 | 0.30 |
| Compound [II'] + DAI | $10^{-4}$ | 1.02 | 1.33 |

FIU: 5-fluoro-2',3'-isopropyrdene uridine
DAI: 2',3'-di-O—acetylinosine
[a]These are the results of a typical experiment.

As shown in Table 1, Con A-induced increase of DNA synthesis of lympocytes was significantly enhanced by compounds [Ex. 8] ($10^{-5}$ M) and [Ex. 9] ($10^{-4}$ M). FIU, a component of compound [Ex. 8] and DAI, that of compound [Ex. 9], did not induce any increase of DNA synthesis in Con A-stimulated lymphocytes. Almost complete inhibition of [6-$^3$H]thymidine incorporation was observed in FIU ($10^{-5}$ M)-treated culture. Compound [II'], a common component of compounds [Ex. 8] and [Ex. 9], seemed to induce an increase of DNA synthesis, but the rate of increase was not significant. Furthermore, the mixture of compound [II'] ($10^{-5}$ M) and FIU ($10^{-5}$ M), or the mixture of compound [II'] ($10^{-4}$ M) and DAI ($10^{-4}$ M) exerted the same effect as that of FIU or DAI alone on the DNA synthesis of Con A-stimulated lymphocytes. Compounds [Ex. 8] and [Ex. 9] enhanced DNA synthesis of lymphocytes even when cultured without Con A (Table I).

(ii) Effect on immuno globulin synthesis of murine splenic lymphocytes

We furthermore investigated the effect of N-acetylneuraminic acid derivatives having T cell activation effect on immuno globulin synthesis by measuring the number of plaque forming cells (PFC). To do this, SPC was cultured together with sheep red blood cells (SRBC) and each of the compounds [I] at 37° C. for 5 days. Then, SRBC and a complement were further added to the sensitized SPC. The resultant sample was cultured in cun'ningham chamber at 37° C. for 3 to 12 hours and then the number of PFC was determined.

It was found that the number of PFC was reduced and the cell viability was identical to the control (free of the compound [I]). This means that the suppressive effect on immuno globulin synthesis is enhanced by the compounds of the formula [I].

TABLE 2

Effect of disaccharide nucleosides and their starting materials on the primary PFC response to SRBC in Vitro

| Treatment | Concentration (M) | PFC/2 × 10$^6$ cultured lymphocytes[a] |
| --- | --- | --- |
| None | — | 57 ± 4 |
| FIU | 10$^{-5}$ | 11 ± 3 |
| DAI | 10$^{-4}$ | 28 ± 6 |
| Compound [II'] | 10$^{-4}$ | 43 ± 11 |
| Compound [Ex. 8] | 10$^{-5}$ | 16 ± 2 |
| Compound [Ex. 9] | 10$^{-4}$ | 25 ± 17 |

[a]Mean ± S.E. of triplicate cultures.

From the result shown in Table 2, the compounds of the examples 8 and 9 and their starting materials induced the decrease of PFC response to SRBC.

Con A-stimulated lymphocytes showed the suppressor activity on the primary PFC response to SRBC. This induction of suppressor cells by Con A was significantly enhanced by the presence of compound [Ex. 8] (10$^{-5}$ M) and compound [Ex. 9] (10$^{-4}$ M) during the incubation with Con A. Furthermore, SPC precultured with compound [Ex. 8] or [Ex. 9] in the absence of Con A also exhibited the suppressor activity. On the other hand, FIU, DAI and compound [II'] did not induce the suppressor activity of the cells (Table 3).

The induction of suppressor cells by compounds [Ex. 8] and [Ex. 9] was abolished by the pretreatment of lymphocytes with anti Thy-1 antiserum plus complement. These results suggest that these disaccharide nucleosides can induce suppressor T cells.

TABLE 3

Effect of the treatment of Con A-stimulated and non-stimulated cells with disaccharide nucleosides on the suppressor activity of the cells

| Treatment[a] | PFC/2 × 10$^6$ cultured lymphocytes[b] | | |
| --- | --- | --- | --- |
| | Exp. 1 | Exp. 2 | Exp. 3 |
| None (Control) | 103 ± 17 | 111 ± 4 | 130 ± 16 |
| FIU (10$^{-5}$ M) | — | — | 108 ± 10 |
| DAI (10$^{-4}$ M) | — | — | 108 ± 8 |
| Compound [II'] (10$^{-4}$ M) | — | — | 145 ± 24 |
| Compound [Ex. 8] (10$^{-5}$ M) | 83 ± 16 | 54 ± 2 | 72 ± 5 |
| Compound [Ex. 9] (10$^{-4}$ M) | 67 ± 9 | 34 ± 7 | 89 ± 17 |
| Con A (2 g/ml) | 68 ± 3 | 65 ± 8 | — |
| [Ex. 8] + Con A | 51 ± 6 | 39 ± 13 | — |
| [Ex. 9] + Con A | 29 ± 9 | 27 ± 8 | — |

[a]2 × 10$^5$ lymphocytes were incubated with disaccharide nucleosides and their starting materials in the presence or absence of Con A at 37° C. for 45 hr, and then the cells were co-cultured with normal fresh spleen cells (2 × 10$^6$ cells) plus SRBC (1 × 10$^6$ cells).
[b]Mean ± S.E. of triplicate cultures.

Up to date, it has been recognized that the function of suppressor T cell is reduced in the case of autoimmune disease such as collagen disease. Therefore, N-acetylneuraminic acid derivatives having activation effect on the suppressor T cell, according to the present invention may be expected to have clinical effectiveness as an immunity control agent.

Now, the present invention will be explained more concretely referring to the following examples. However, these examples merely explain the present invention and they do not limit the present invention.

EXAMPLE 1

Praparation of 2',3'-di-O-acetyl-5'-O-(4-N-acetyl-2,4-dideoxy-3,6,7,8-tetra-O-acetyl-1-methoxycarbonyl-D-glycero-α-D-galacto-octopyranosyl) inosine To 30 ml of acetonitrile, 550 mg of 2',3'-di-O-acetylinosine, 150 mg of Hg(CN)$_2$, 300 mg of HgBr$_2$ and 500 mg of molecular sieve (4A) were added, further 510 mg of methyl 2-chloro-4,7,8,9-tetra-O-acetyl- -D-N-acetylneuraminate (compound [II']) was added to said mixture and the mixture was agitated at room temperature for 48 hours. The resultant solution was filtered and the filtrate was evaporated to dryness. To the residue, 50 ml of ethyl acetate was added and the solution was washed two times with 30% potassium iodide solution to remove Hg(CN)$_2$ and HgBr$_2$. The solution was dried over Glauber's salt and the solvent was distilled off. Purification was established by subjecting the crude product to alumina column chromatography and eluting with benzeneethylacetate. The title compound was obtained in an amount of 430 mg (yield 52%) as colorless powder.

Physical properties: $[\alpha]_D^{25}$: $-61°$ C. (c=1, methanol).

Elemental Analysis: C$_{34}$H$_{43}$N$_5$O$_{19}$; calculated: C: 49.46; H: 5.25; N: 8.48; found: C: 49.15; H: 5.41; N: 8.11.

Mass Spectroscopy (FD) m/z: 825 (M+).

I.R.$\nu_{max}^{KBr}$ (cm$^{-1}$) 3300, 1740, 1660, 1530.

$^1$H NMR (CDCl$_3$)δH$_H$(TMS) 1.88–2.20 (OAcx7), 2.76 (1H, dd, J=13.0 and 4.5 Hz); 3.78 (3H, s), 5.95 (1H, d, J=2.2 Hz); 8.20 (1H, s), 8.44 (1H, s).

EXAMPLE 2

Preparation of 2',3'-isopropylidene-5'-O-(4-N-acetyl-2,4-dideoxy-3,6,7,8-tetra-O-acetyl-1-methoxycarbonyl-D-glycero-α-D-galacto-octopyranosyl) uridine To a mixture of 1 g of 2',3'-isopropylideneuridine, 150 mg of Hg(CN)$_2$ and 300 mg of HgBr$_2$, 50 ml of acetonitrile was added and further 1 g of molecular sieve (4 A) was added.

The mixture was reacted with 510 mg of the compound [II'] under agitation at room temperature for 24 hours. The solution obtained was filtered and the filtrate was evaporated to dryness at 40° C. under reduced pressure to remove the solvent. To the residue, 100 ml of ethylacetate was added and the solution was washed with 30% potassium iodide solution to remove Hg(CN)$_2$ and HgBr$_2$. The ethylacetate solution was dried over Glauber's salt, the solvent was removed and oily material was obtained. From the oily material, substances soluble in ether were removed and after the addition of 10 ml of chloroform non-soluble material was removed. By the addition of ether to the chloroform solution, precipitates were formed and filtered off, dried. Thus, 300 mg (yield 40%) of colorless powder was obtained.

Physical properties: $[\alpha]_D^{22}$: $-2.1°$ (c=1, methanol).

Elemental Analysis: C$_{32}$H$_{43}$N$_3$O$_{18}$; MW=757.70; calculated: C: 50.73; H: 5.72; N: 5.55; found: C: 50.56; H: 5.90; N: 5.22.

Mass Spectroscopy: m/z: 757(M+), 742(M+−15); 714(M+−43), 698 (M+−59).

I.R. $\nu_{max}^{KBr}$ (cm$^{-1}$): 1735, 1678, 1530.

$^1$H NMR (CDCl$_3$)$\delta_H$(TMS): 1.48 (s, 3H), 1.70(s, 3H), 1.88 (s, 3H), 2.00–2.20(OAcx4), 2.60(dd, 1H, J=4.0 and 13.0 Hz) 3.80(s, 3H), 5.68(d, 1H, J=7.0 Hz), 7.60(d, 1H, J=7.0 Hz).

EXAMPLE 3

Preparation of 2′,3′-isopropylidene-5′-O-(4-N-acetyl-2,4-dideoxy-1-methoxycarbonyl-D-glycero-α-D-galacto-octapyranosyl) uiridine The compound obtained from Example 3 was dissolved in 10 ml methanol, the solution was reacted with a solution prepared by dissolving 100 mg of metal potassium in 10 ml of methanol and the resultant solution was agitated at 0° C. for 20 minutes. The solution was neutralized with Dowex 50×8 (H+) at −20° C., filtered, concentrated, evaporated to dryness. The resultant residue was dissolved in 5 ml of methanol, dioxane was further added to precipitate and filtered. Thus, 230 mg (yield 60%) of colorless powder was obtained.

Physical properties: $[\alpha]_D^{20}$ −9.5° (c=1, H$_2$O).

Elemental Analysis: C$_{24}$H$_{35}$N$_3$O$_{14}$, MW=589,55; calculated: C: 48.89; H: 5.98; N: 7.13; found: C: 48.25; H: 6.03; N: 7.05.

I.R. $\nu_{max}^{KBr}$ (cm$^{-1}$): 3300, 1735, 1645, 1530.

$^1$H NMR (D$_2$O) $\delta_H$ (DSS); 1.55(s, 3H), 1.66(s, 3H), 2.30(s, 3H), 3.4(s, 3H), 5.96(d, 1H, J=8.5 Hz), 5.99(d, 1H, J=1.2 Hz), 7.90(d, 1H, J=8.5 Hz).

EXAMPLE 4

Preparation of methyl 1′,2′,3′,4′-tetra-O-acetyl-β-D-glucopyranosyl-(6′→2)-4,7,8,9-tetra-O-acetyl-α-D-N-acetylneuraminate 1,2,3,4-tetra-O-acetyl-β-D-glucopyranose 1.5 g was dissolved in 50 ml of acetonitrile and to the solution, 1 g of molecular sieve (4 A), 150 mg of Hg(CN)$_2$ and 300 mg of HgBr$_2$ were added and further 1 g of the compound [II′] was added. The resultant solution was stirred at room temperature for 12 hours and then filtered. The filtrate was distilled at 40° C. under reduced pressure to remove solvent and evaporated to dryness. To the residue obtained, 100 ml of ethylacetate was added and the solution was washed with 30% potassium iodide aqueous solution to remove Hg(CN)$_2$ and HgBr$_2$. The resulting ethylacetate solution was dried over Glauber's salt and then the solvent was distilled off. The remaining powder was subjected to silica gel column chromatography and eluted by a mixed benzene-ethylacetate solvent to purify the product. Thus, 650 mg (yield 40%) of colorless powder was obtained.

Physical properties: $[\alpha]_D^{24}$+3.2° (c=1, methanol).

Elemental Analysis: C$_{34}$H$_{47}$NO$_{22}$, MW=821.74; calculated: C: 49.70; H: 5.77; N: 1.71; found: C: 49.02; H: 5.52; N: 1.40.

Mass Spectroscopy: m/z; 821(M+), 762(M+−59).

I.R. $\nu_{max}^{KBr}$ (cm$^{-1}$): 1735, 1655, 1530.

$^1$H NMR (CDCl$_3$)$\delta_H$(TMS); 1.89(s, 3H), 1.99–2.12(OAcx8), 3.74(s, 3H).

EXAMPLE 5

Preparation of methyl D-glucopyranosyl-(6′→2)-α-D-N-acetylneuraminate

The compound obtained in Example 5 (500 mg) was dissolved in 10 ml of methanol, to the solution a solution of 100 mg of metal potassium in 10 ml methanol was added and stirred at 0° C. for 20 minutes. The solution was neutralized with Dowex 50×8(H+); filtered, concentrated and evaporated to dryness and then the resultant residue was dissolved in 5 ml of ethanol and ether was added to precipitate. The precipitates were filtered off and 220 mg (yield 75%) of colorless powder was obtained.

Physical properties: $[\alpha]_D^{20}$ +25° (c=1, H$_2$O).

Elemental Analysis: C$_{18}$H$_{31}$NO$_{14}$, MW=485.44; calculated: C: 44.54; H: 6.44; N: 2.89; found: C: 44.15; H: 6.42; N: 2.52.

I.R. $\nu_{max}^{KBr}$ (cm$^{-1}$): 3300, 1735, 1645, 1530.

$^1$H NMR (D$_2$O)$\delta_H$(DSS): 2.05 (s, 3H), 3.85 (s, 3H).

EXAMPLE 6

Preparation of 5′-O-(4-N-acetyl-2,4-dideoxy-1-methoxycarbonyl-D-glycero-α-D-galacto-octopyranosyl)inosine

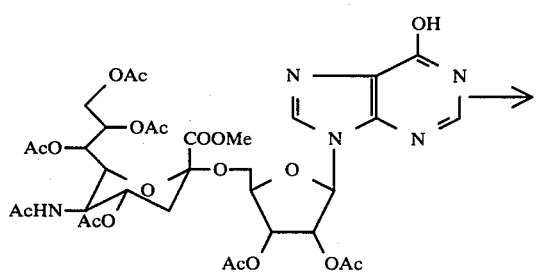

[A]

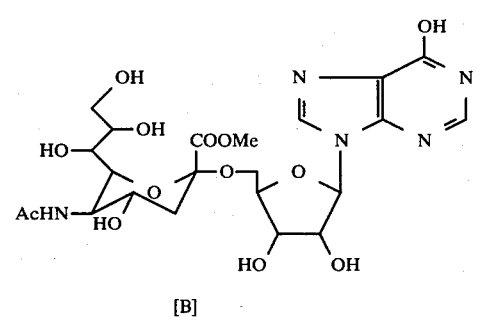

[B]

The compound [A] 300 mg was dissolved in 10 ml of methanol, to this solution a solution of 80 mg metal potassium in 10 ml of methanol was added and the resulting solution was stirred at 0° C. for 20 minutes, thereafter the solution was neutralized with the addition of Dowex 50×8(H+) at −20° C. The neutralized solution was filtered, concentrated and evaporated to dryness. The residue thus obtained was dissolved in 1 ml of water and ethanol was added to the solution to separate out the precipitate. As a result, 150 mg (yield 71%) of the compound [B] was obtained as colorless powder.

Physical properties: $[\alpha]_D^{20}$ −22° (c=1, H$_2$O).

Elemental Analysis: C$_{22}$H$_{31}$N$_5$O$_{13}$, MW=573; calculated: C: 46.07; H: 5.45; N: 12.21; found: C: 45.65; H: 5.61; N: 12.18.

I.R. $\nu_{max}^{KBr}$ (cm$^{-1}$): 3300, 1735, 1655, 1530.

$^1$H NMR (D$_2$O)$\delta_H$(DSS): 2.05(s, 3H), 3.85(s, 3H); 8.15(s, 1H), 8,62(s, 1H).

EXAMPLE 7

Preparation of 5-fluoro-2',3'-isopropylidene-5'-O-(4-N-acetyl-2,4-dideoxy-1-methoxycarbonyl-D-glycero-α-D-galacto-octopyranosyl) uridine:

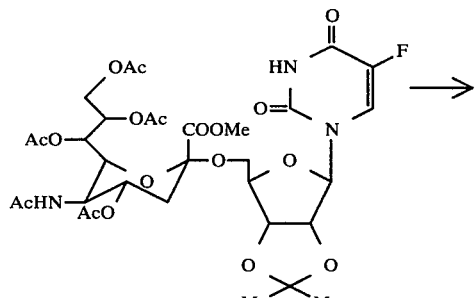

[C]

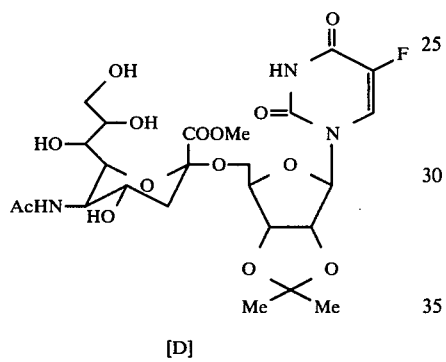

[D]

A solution obtained by dissolving 500 mg of the compound [C] in 10 ml of methanol was reacted with a solution of 100 mg metal potassium in 10 ml of methanol and stirred at 0° C. for 20 minutes. To the solution Dowex 50×8(H+) was added at −20° C. to neutralize it and the solution was filtered, concentrated, evaporated to dryness and then the resultant residue was dissolved in 5 ml of methanol and added dioxane to separate out the precipitate. The precipitate was separated out from the solvent and the compound [D] was obtained in an amount of 180 mg (yield 48%) as colorless powder.

Physical properties: $[\alpha]_D^{20}$ −1.1° (c=1, methanol).

Elemental Analysis: $C_{24}H_{34}N_3O_{14}F$, MW=607; calculated: C: 47.45; H: 5.60; N: 6.92; found: C: 47.92; H: 5.45; N: 6.21.

I.R. $\nu_{max}^{KBr}$ (cm$^{-1}$): 3300, 1735, 1640, 1535.

EXAMPLE 8

Preparation of 5-fluoro-2',3'-isopropylidene-5'-O-(4-N-acetyl-2,4-dideoxy-3,6,7,8-tetra-O-acetyl-1-methoxycarbonyl-D-glycero-α-D-galacto-octopyranosyl)-uridine Compound [II'] +

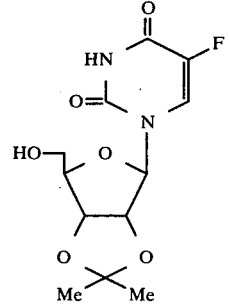

[E]

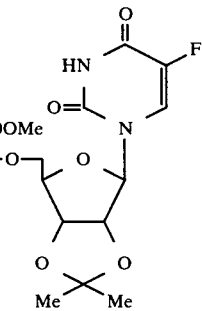

[F]

Method (i)

On 30 ml of CH$_3$CN, 500 mg of 5-fluoro-2',3'-isopropylideneuiridine [E], 150 mg of Hg(CN)$_2$ and 300 mg of HgBr$_2$ were dissolved and further 1 g of powdery molecular sieve (3A) was added. After 1 hour agitation, 510 mg of the compound [II'] was introduced and the solution was stirred at room temperature over 24 hours. The resulting solution was filtered and the solvent of the filtrate was distilled off at 40° C. under reduced pressure to be evaporated to dryness. The residue obtained was dissolved in 100 ml of ethylacetate and washed with the aid of 30% potassium iodide aqueous solution to remove Hg(CN)$_2$ and HgBr$_2$. The ethylacetate phase was dried over Glauber's salt and the solvent was distilled off to obtain oily substance. From the oil, ether soluble substances were removed and 10 ml of chloroform was added to remove chloroform insoluble materials. To the chloroform solution thus obtained, ether was added to separate out precipitates. The precipitates were purified by subjecting them to alumina column chromatography and eluting with ethylacetate-ethanol mixture. Thus, 62 mg (yield 8%) of the compound [F] was obtained as colorless powder.

Physical properties: $[\alpha]_D^{25}$ −1.4° (c=1, methanol).

Elemental Analysis: $C_{32}H_{42}N_3O_{18}F$; calculated: C: 49.55; H: 5.42; N: 5.45; found: C: 49.24; H: 5.80; N: 5.12.

Mass Spectroscopy m/z: 775(M+), 760(M+ −Me),

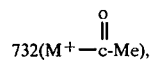

732(M+ −c-Me),

716(M+ −COOMe).

I.R. $\nu_{max}^{KBr}$ (cm$^{-1}$): 1735, 1680, 1530

$^1$H NMR (CDCl$_3$)$\delta_H$(TMS):

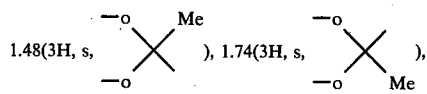

1.89–2.20(15H, all s, —NHAc and —OAc), 2.63(1H, dd, J=4.0 and 14.0 Hz, 3″—H eq.) 3.80(3H, s, methylester), 5.95(1H, d, J=2.0 Hz, 1′—H), 7.62(1H, d, J=7 Hz, 6—H).

Method (ii)

The compound [E] (500 mg) was dissolved in 10 ml of $CH_3NO_2$, then 350 mg of $AgClO_4$ and 200 mg of powdered molecular sieve (4A) were added and the mixture was stirred for 30 minutes. Then, a solution of 510 mg of the compound [II′] in 5 ml of $CH_3NO_2$ was added to the mixture and the resulting solution was stirred at room temperature for 2 hours. The resultant solution was filtered and 50 ml of ethylacetate was added to the filtrate and to the solution, 20 ml of saturated sodium chloride solution was introduced. The $CH_3NO_2$-ethylacetate solution was dried over Glauber's salt and after filtration of the solution the solvent was distilled off. The residue was extracted by ether to remove ether-soluble substances and then extracted by chloroform to remove chloroform-insoluble materials. To the resulting chloroform solution ether was added to separate out precipitates. The precipitates were purified by subjecting them to alumina column chromatography and eluting them with ethylacetate-ethanol mixed solvent and thus 150 mg (yield 20%) of the compound [F] was obtained as colorless powder.

EXAMPLE 9

Preparation of 2′,3′-di-O-acetyl-5′-O-(4-N-acetyl-2,4-dideoxy-3,6,7,8-tetra-O-acetyl-1-methoxycarbonyl-D-glycero-α-D-galacto-octopyranosyl) inosine Compound [II′] +

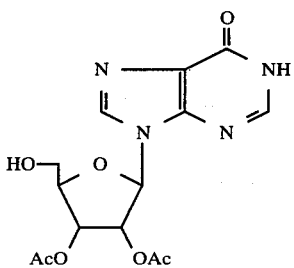

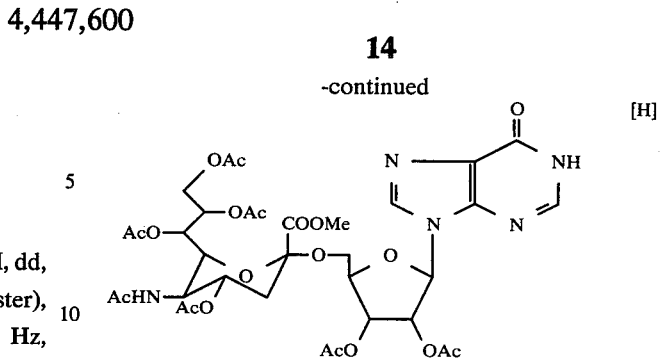

Adding 550 mg of the compound [G], 150 mg of $Hg(CN)_2$, 300 mg of $HgBr_2$ and 500 mg of powdered molecular sieve (4 A) to 30 ml of $CH_3CN$, the resulting mixture was agitated for 1 hour. Then, introducing 510 mg of the compound [II′] into the mixture, the resulting solution was stirred at room temperature for 48 hours to react with each other. The reaction solution was filtered, the filtrate was concentrated and evaporated to dryness. The residue obtained was dissolved in 50 ml of ethylacetate and the solution was washed twice with the aid of 30% potassium iodide to remove $Hg(CN)_2$ and $HgBr_2$. Then, the ethylacetate solution was dried over Glauber's salt and the solution was distilled to remove solvent. The oily material resulting from said distillation was subjected to alumina column chromatography by using benzene-ethylacetate-ethanol to purify the product and thus 210 mg (yield 25%) of the title compound was obtained as colorless powder.

Physical properties: $[\alpha]_D^{25} -16°$ (c=1, methanol).
Elemental Analysis: $C_{34}H_{43}N_5O_{19}$; calculated: C: 49.46; H: 5.25; N: 8.48; found: C: 49.15; H: 5.41; N: 8.11.
Mass Spectroscopy (FD): m/z 825(M+).
I.R. $\nu_{max}^{KBr}$ (cm$^{-1}$): 3300, 1740, 1660, 1530.
$^1$H NMR $(CDCl_3)\delta_H(TMS)$: 1.88–2.20(21H, all s, NHAc and OAcx6) 2.76(1H, dd, J=13.0 and 4.5 Hz, 3-Heq) 3.78(3H, s, methylester), 5.95(1H, s, J=2.2 Hz, 1′—H), 8.20(1H, s, 2—H), 8.44(1H, s, 6—H).

What is claimed is:

1. N-acetylneuraminic acid derivatives of the general formula (I):

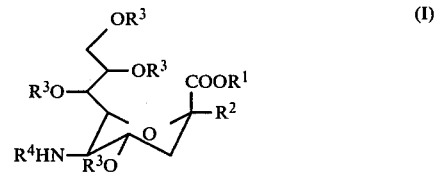

wherein $R^1$ represents hydrogen, lower alkyl or a lower alkyl substituted or non-substituted aralkyl or aryl group, $R^2$ is a nucleoside residue and $R^3$ and $R^4$ independently represent hydrogen or acetyl.

2. N-acetylneuraminic acid derivative as set forth in claim 1 wherein $R^2$ is the residue of 5-fluoro-2′,3′-isopropylideneuiridine and $R^3$ and $R^4$ are acetyl.

3. N-acetylneuraminic acid derivative as set forth in claim 1 wherein $R^1$ is methyl, $R^2$ is the residue of 2′,3′-di-O-acetylinosine and $R^3$ and $R^4$ are acetyl.

4. N-acetylneuraminic acid derivative as set forth in claim 1 wherein $R^1$ is methyl, $R^2$ is the residue of 2′,3′-isopropylideneuridine, $R^3$ is hydrogen and $R^4$ is acetyl.

5. N-acetylneuraminic acid derivative as set forth in claim 1 wherein $R^1$ is methyl group, $R^2$ is the residue of 2′,3′-isopropylideneuiridine and $R^3$ and $R^4$ are acetyl group.

* * * * *